US012740968B2

(12) United States Patent
Vince et al.

(10) Patent No.: US 12,740,968 B2
(45) Date of Patent: Sep. 22, 2026

(54) METHODS FOR THE TREATMENT OF CONDITIONS RELATED TO HYDROGEN SULFIDE

(71) Applicant: Regents of the University of Minnesota, Minneapolis, MN (US)

(72) Inventors: Robert Vince, Minneapolis, MN (US); Swati Sudhakar More, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/441,087

(22) Filed: Feb. 14, 2024

(65) Prior Publication Data

US 2025/0017909 A1 Jan. 16, 2025

Related U.S. Application Data

(63) Continuation of application No. 17/381,308, filed on Jul. 21, 2021, now Pat. No. 11,925,623.

(60) Provisional application No. 63/054,631, filed on Jul. 21, 2020.

(51) Int. Cl.

| | |
|---|---|
| ***A61K 31/426*** | (2006.01) |
| ***A61K 31/198*** | (2006.01) |
| ***A61K 31/22*** | (2006.01) |
| ***A61K 31/265*** | (2006.01) |
| ***A61K 31/385*** | (2006.01) |
| ***A61K 31/554*** | (2006.01) |
| ***A61P 25/28*** | (2006.01) |

(52) U.S. Cl.

CPC .......... *A61K 31/426* (2013.01); *A61K 31/198* (2013.01); *A61K 31/22* (2013.01); *A61K 31/265* (2013.01); *A61K 31/385* (2013.01); *A61K 31/554* (2013.01); *A61P 25/28* (2018.01)

(58) Field of Classification Search

None

See application file for complete search history.

(56) References Cited

U.S. PATENT DOCUMENTS

| | | | |
|---|---|---|---|
| 5,834,448 | A | 11/1998 | Pouchol et al. |
| 6,274,564 | B1 | 8/2001 | Sarill et al. |
| 8,757,354 | B2 | 6/2014 | Hazenbroek |
| 9,757,354 | B2 | 9/2017 | Patterson et al. |
| 11,925,623 | B2 | 3/2024 | Vince et al. |
| 2009/0197865 | A1 | 8/2009 | Nagasawa et al. |
| 2012/0329731 | A1 | 12/2012 | Nagasawa et al. |
| 2016/0354341 | A1 | 12/2016 | Patterson et al. |
| 2018/0118674 | A1 | 5/2018 | Wang et al. |

FOREIGN PATENT DOCUMENTS

| | | | |
|---|---|---|---|
| WO | 2008005806 | A2 | 1/2008 |
| WO | 2011133893 | A2 | 10/2011 |

OTHER PUBLICATIONS

Palmer, Alan. The Role of the Blood Brain Barrier in Neurodegenerative Disorders and their Treatment. Jn of Alzheimer's Disease 2011 24:4, 643-656. (Year: 2011).*

Banks et al. Delivery of drugs through the blood-brain barrier: need for trials. The Lancet Neurology, published 2025. (Year: 2025).*

Sawaya A, Regina AC, Menezes RG. Hydrogen Sulfide Toxicity. [Updated May 2, 2024]. In: StatPearls [Internet]. Treasure Island (FL): StatPearls Publishing; Jan. 2025. (Year: 2025).*

Alarie, Y , "Toxicity of Fire Smoke", Critical Reviews in Toxicology vol. 32 (4), 259-289 (2008).

Baskin , "In Vitro and In Vivo Comparison of Sulfur Donors as Antidotes to Acute Cyanide Intoxification", J. Appl. Toxicol., 19, 173-183 (1999).

Baud, F , et al., "Elevated blood cyanide concentrations in victims of smoke inhalation", The New England Journal of Medicine 325(25), 1761-1766 (1991).

Beaumont, K , et al., "Design of Ester Prodrugs to Enhance Oral Absorption of Poorly Permeable Compounds: Challenges to the Discovery Scientist", Current Drug Metabolism 4, 461-485 (2003).

Belani, K , et al., "Cyanide toxicity in juvenile pigs and its reversal by a new prodrug, sulfanegen sodium", Anesth Analg 114, 956-961 (2012).

Brenner, M. , "Acceleration of Advanced CN Antidote Agents for Mass Exposure Treatments: DMTS", Grants Award No. W81XWH-12-2-0098, 12 pg., (Sep. 25-26, 2013).

Brenner, M , et al., "Sulfanegen sodium treatment in a rabbit model of sub-lethal cyanide toxicity", Toxicol Appl Pharmacol 248, 269-276 (2010).

Cabral-Costa, J , et al., "Neurological disorders and mitochondria", Molecular Aspects of Medicine 71, 100826 (2020).

Cavallini , "The Oxidation of Sulfur-Containing Amino Acids by L-Amino Acid Oxidases", Advances in Experimental Medicine and Biology, 148, 359-374, (1982).

Chan, A. , et al., "The combination of cobinamide and sulfanegen is highly effective in mouse models of cyanide poisoning", Clin Toxicol 49(5), 16 pages (2011).

Chen, X , et al., "Oxidative stress in neurodegenerative diseases", Neural Regeneration Research 7(5), 376-385 (2012).

Clemedson , "On the Toxicity of Sodium beta-mercapto pyruvate and Its Antidotal Effect against Cyanide", Acta. Physiol. Scand. 42, 41-45, (1958).

Cooper , "On the Chemistry and Biochemistry of 3-Mercaptopyruvic Acid, the □-Keto Acid Analog of Cysteine", J. Biol. Chem., 257, 816-826, (1982).

Crankshaw, D , et al., "A novel paradigm for assessing efficacies of potential antidotes against neurotoxins in mice", Toxicol Lett 175, 111-117 (2007).

Esposito, F , et al., "Inhalation toxicity of carbon monoxide and hydrogen cyanide gases released during thermal decomposition of polymers", J Fire Sci 6, 195-242 (1988).

Gu, X , et al., "Measurement of mitochondrial respiration in adherent cells by Seahorse XF96 Cell Mito Stress Test", Star Protoc 2(1), 100245, doi:10.1016/j.xpro.2020.100245 (2021).

(Continued)

*Primary Examiner* — Lauren Wells

(74) *Attorney, Agent, or Firm* — Viksnins Harris Padys Malen LLP

(57) ABSTRACT

The invention provides compositions and methods for treating conditions associated with decreased activity of hydrogen sulfide.

8 Claims, 11 Drawing Sheets

(56) References Cited

OTHER PUBLICATIONS

Hu, L. , et al., "Neuroprotective effects of hydrogen sulfide on Parkinson's disease rat models", Aging Cell 9, 135-146 (2010).
Huang, J , et al., "Hepatocyte-Catalysed Detoxification of Cyanide by L- and D-Cysteine", Biochemical Pharmacology, vol. 55, 1983-1990 (1998).
Jarabak, R , "3-Mercaptopyruate Sulfurtransferase (Rhodanese)", Methods in Enzymology, Academic Press (Jakoby, W.B., Ed.), vol. 77, 291-297 (1981).
Koplovitz , "Assessment of Motor Performance Decrement Following Soman Poisoning in Mice", Drug and Chemical Toxicology, 12, 221-235 (1989).
Kwon, H , et al., "Neuroinflammation in neurodegenerative disorders: The roles of microglia and astrocytes", Translational Neurodegeneration 9, 42 (2020).
Meister , "Enzymatic Desulfurization of Mercaptopyruvate to Pyruvate", Journal of Biological Chemistry, 206, 561-575 (1954).
Mishra, A , et al., "Neuroinflammation in neurological disorders: Pharmacotherapeutic targets from bench to bedside", Metabolic Brain Disease 36, 1591-1626 (2021).
Mousa, H , et al., "Alternative Sulphur Donors for Detoxification of Cyanide in the Chicken", Comp Biochem Physiol vol. 99C(3), 309-315 (1991).
Nagahara, N , et al., "Do antidotes for acute cyanide poisoning act on mercaptopyruvate sulfurtransferase to facilitate detoxification?", Curr Drug Targets Immune Endocr Metabol Disord 3, 198-204 (2003).
Nagasawa, H , et al., "Novel, Orally Effective Cyanide Antidotes", J Med Chem 50, 6462-6464 (2007).
Norat, P , et al., "Mitochondrial dysfunction in neurological disorders: Exploring mitochondrial transplantation", NPJ Regenerative Medicine 5, 22, 9 pages (2020).
Olson, K , et al., "The role of hydrogen sulfide in evolution and the evolution of hydrogen sulfide in metabolism and signaling", Physiology (Bethesda, Md.) 31, 60-72 (2016).
Patel, M , "Targeting oxidative stress in central nervous system disorders", Trends in Pharmacological Sciences 37, 768-778 (2016).
Patterson, S , et al., "Cyanide antidotes for mass casualties: water-soluble salts of the dithiane (sulfanegen) from 3-mercaptopyruvate for intramuscular administration", J Med Chem 56, 1346-1349 (2013).
Patterson, S , et al., "Development of sulfanegen for mass cyanide casualties", Ann NY Acad Sci 1374(1), 202-209 (2016).
Paul, B , et al., "Effects of hydrogen sulfide on mitochondrial function and cellular bioenergetics", Redox Biology 38, 101772, 9 pages (2021).
Rao, S , et al., "Sulfanegen stimulates 3-mercaptopyruvate sulfurtransferase activity and ameliorates alzheimer's disease pathology and oxidative stress in vivo", Redox Biology 57, 102484, 14 pages (2022).
Schubert , et al., "Antagonism of Experimental Cyanide Toxicity in Relation to the In Vivo Activity of Cytochrome Oxidase", Journal of Pharmacology and Experimental Therapeutics vol. 162(2), 352-359 (1968).
SciFinder , CAS Registry No. 80003-64-1, American Chemical Society (ACS), 2 pages (2013).
Shibuya, N , et al., "3-Mercaptopyruvate Sulfurtransferase Produces Hydrogen Sulfide and Bound Sulfane Sulfur in the Brain", Antioxidants & Redox Signaling 11(4), 703-714 (2009).
Singh, H , et al., "Stylet-Assisted Tracheal Intubation Through an ILMA in a Patients with an Anterior Larynx", Anesthesiology and Analgesia vol. 115 (2), 480-481 (2012).
Tabassum, R , et al., "Potential for therapeutic use of hydrogen sulfide in oxidative stress-induced neurodegenerative diseases", Int J Med Sci 16(10), 1386-1396, PMID: 31692944 (2019).
Tanabe , "Preparation of a Sulfurtransferase Substrate, Sodium 3-Mercaptopyruvate, from 3-Bromopyruvic acid and Sodium Hydrosulfide", Chem. Pharm. Bull., 37, 2843-2845 (1989).
Testa, B , "Prodrug research: futile or fertile?", Biochemical Pharmacology 68, 2097-2106 (2004).
Tomita, M , et al., "Expression of 3-mercaptopyruvate sulfurtransferase in the mouse", Molecules 21, 1707, 8 pages (2016).
Tulsawani , "Effect of sub-acute oral cyanide administration in rats: Protective efficacy of alpha-ketoglutarate and sodium thiosulfate", Chemico-Biological Interactions, 156, 1-12, (2005).
Wang, W , et al., "Mitochondria dysfunction in the pathogenesis of alzheimer's disease: Recent advances", Molecular Neurodegeneration 15, 30 (2020).
Way , "Cyanide Antagonism with Mercaptopyruvate", Federation Proceedings 44(3), 1797 (1985).
Westley, J , "Rhodanse and the Sulfane Pool", Enzymatic Basis of Detoxification, vol. 2, Jakoby, W.B. Ed., 245-259 (1980).
Westley, J , "Thiosulfate: Cyanide Sulfurtransferase (Rhodanese)", Methods in Enzymology, Academic Press, Jakoby, W.B. Ed., 77, 285-291 (1981).
Wolff , "Burger's Medicinal Chemistry and Drug Discovery", Fifth Edition, vol. 1: Principles and Practice, 975-977 (1995).
Xuan, A , et al., "Hydrogen sulfide attenuates spatial memory impairment and hippocampal neuroinflammation in β-amyloid rat model of Alzheimer's disease", J Neuroinflammation 9 (202), 11 pages, PMID: 22898621 (2012).
Yusuf, M , et al., "Biomechanistic insights into the roles of oxidative stress in generating complex neurological disorders", Biological Chemistry 399 (4), 305-319 (2018).
Zhang, J , et al., "Hydrogen sulfide therapy in brain diseases: from bench to bedside", Med Gas Res 7(2), 113-119, PMID: 28744364 (2017).

* cited by examiner

A

B

C

METHODS FOR THE TREATMENT OF CONDITIONS RELATED TO HYDROGEN SULFIDE

CROSS-REFERENCE TO RELATED APPLICATION

This patent application is a Continuation of U.S. application Ser. No. 17/381,308, filed Jul. 21, 2021, which claims the benefit of priority of U.S. Provisional Application No. 63/054,631, filed Jul. 21, 2020, which application is herein incorporated by reference.

BACKGROUND

Alzheimer's disease (AD) is the most common progressive neurodegenerative disease responsible for cognitive impairment in elderly subjects. In AD, loss of neurons in the cerebral cortex and hippocampus is accompanied by extracellular deposition of Aβ plaques and neurofibrillarytangles of hyperphosphorylated tau. Currently, other than symptomatic therapies to maintain cerebrocortical activity and to modulate learning/cognition, there are no ways to stop the progression of the disease. Given the increased prevalence of the disease, there is an urgent need to develop therapies that can stop or slow down the progression of AD. Increased oxidative stress and inflammation are implicated in the onset and progression of AD. Traditional antioxidants and anti-inflammatory therapies have shown promise in preclinical studies, but have produced mixed results in clinical testing. Novel and more specific targets are needed to address AD-related pathological changes.

Hydrogen sulfide ($H_2S$) is endogenously produced in the brain from amino acid cysteine. Numerous studies have shown its antioxidant, anti-inflammatory and anti-apoptotic effects in neurons and glial cells. Brain levels of $H_2S$ are severely reduced in AD patients compared to age matched normal subjects. Levels and activities of enzymes involved in endogenous $H_2S$ production, such as cystathionine beta-synthase (CBS) and 3-mercaptopyruvate sulfurtransferase (3-MST), are reduced as AD progresses. Supplementation of $H_2S$ and its donors have shown beneficial effects on AD pathology by reducing neuroinflammation and oxidative stress, preserving glutathione homeostasis and reducing the levels of reactive aldehydes. [Xuan, A., et al., *Journal of Neuroinflammation* 2012, 9:202, Zhang H., et al. *Med. Gas Res.* 2017, 7(2), 113-119, Tabassum R., et al., *Int. J. Med. Sci.* 2019, 16(10), 1386-1396].

The endogenous substrate for 3-MST is the deaminated cysteine catabolite, 3-mercaptopyruvate (3-MP, 1) however the poor stability of 3-MP renders this substrate a poor drug candidate. International Patent Application Publication Number WO 2008/005806 and Nagahara, N., et al., *Curr. Drug Targets Immune Endocr. Metabol. Disord* 2003, 3, 198-204. Thus, some efforts have focused on developing prodrugs of 3-MP. Nagasawa, H. T., et al., *J. Med Chem.* 2007, 50, 6462-6464; Patterson, S. E., et al., *J. Med Chem.* 2013, 56, 1346-1349; Singh, H., et al., *Anesthesiology and Analgesia* 2012, in press; Chan, A., et al., *Clin. Toxicol. (Phila.)* 2011, 49, 366-373; and Brenner, M., et al., *Toxicol. Appl. Pharmacol.* 2010, 248, 269-276.

1

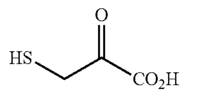

-continued

2

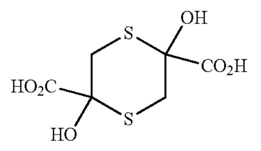

Mercaptopyruvic acid (1, 3-MP), the endogenous substrate for 3-MST and its dithiane form (2).

The dithiane form of 3-MP (sulfanegenic acid, 2), as a sodium salt has been shown to be highly effective in rescue of sublethal murine and lethal swine models of cyanide toxicity when administered intraperitoneally (ip) and iv. Nagasawa, H. T., et al., *J. Med Chem.* 2007, 50, 6462-6464; Belani, K. G., et al., *Anesth. Analg.* 2012, 114, 956-961; and Crankshaw, D. L., et al., *Toxicol. Lett.* 2007, 175, 111-117. Additionally, sulfanegen triethanolamine has been investigated for treating cyanide toxicity. Patterson, S. E., et al., *J. Med Chem.* 2013, 56, 1346-1349. Unfortunately, this sulfanegen salt has poor thermal stability with a short (<6 month) shelf life at room temperature (unpublished results). Prodrugs of 3-MP when administered ip or orally in mice subjected to toxic, but nonlethal dose of cyanide, reduced the average righting reflex times (a measure of cyanide antidote efficacy) compared to placebo-treated mice. [PMID: 27308865]

U.S. Pat. No. 8,757,354 provides sulfanegen salts and methods for treating cyanide poisoning. Several sulfanegen salts were found to be water soluble and orally available. The salts were effective as antidotes against cyanide poisoning in lethal and sublethal animal models.

Currently there is a continuing need for methods that are effective to treat diseases and conditions that are associated with decreased activity of $H_2S$, including neurodegenerative diseases, such as Alzheimer's disease.

SUMMARY

Applicant evaluated sulfanegen in acute intracerebroventricular (icv) amyloid-beta mouse model of Alzheimer's disease. Intraperitoneal administration of sulfanegen (50 and 100 mg/kg) prevented cognitive impairment caused by amyloid-beta peptide in this mouse model as determined by the T-maze assay. Sulfanegen-treated mice did not exhibit spatial bias or anxiety-like behavior in this cognitive test.

Accordingly, in one embodiment, the invention provides a method comprising, treating a disease or condition that is associated with decreased activity of $H_2S$ in an animal in need thereof, by administering to the animal, an effective amount of a compound or a pharmaceutically acceptable salt that releases 3-mercaptopyruvate in the animal In another embodiment, the invention provides a compound or a pharmaceutically acceptable salt that releases 3-mercaptopyruvate for the prophylactic or therapeutic treatment of a disease or condition that is associated with decreased activity of $H_2S$.

In another embodiment, the invention provides the use of a compound or a pharmaceutically acceptable salt that releases 3-mercaptopyruvate for the preparation of a medicament useful for treating a disease or condition that is associated with decreased activity of $H_2S$ in an animal.

In another embodiment, the invention provides a method comprising, administering an effective $H_2S$ producing amount of a compound or a pharmaceutically acceptable salt that releases 3-mercaptopyruvate to an animal that has been identified as having a disease or condition associated with decreased activity of $H_2S$.

In another embodiment, the invention provides a kit comprising: a) a compound or a pharmaceutically acceptable salt that releases 3-mercaptopyruvate in vivo; b) instructions for administering the compound or the pharmaceutically acceptable salt to treat a disease or condition that is associated with decreased activity of $H_2S$ in an animal; and c) packaging material that contains the compound or the pharmaceutically acceptable salt and the instructions.

In another embodiment, the invention provides a kit comprising a) sulfanegen or a pharmaceutically acceptable salt thereof; b) instructions for administering sulfanegen or the pharmaceutically acceptable salt thereof to treat a disease or condition that is associated with decreased activity of $H_2S$ in an animal; and c) packaging material that contains the sulfanegen or the pharmaceutically acceptable salt thereof and the instructions.

BRIEF DESCRIPTION OF THE FIGURES

FIG. 8A shows data from Example 7. FIG. 8B shows data from Example 6. FIG. 8C shows data from Example 5. The 100 mg/kg dose of sulfangen showed toxicity in animals as observed by elevations in liver and kidney enzymes in 2 animals (total N=8/group).

DETAILED DESCRIPTION

Figure 1:
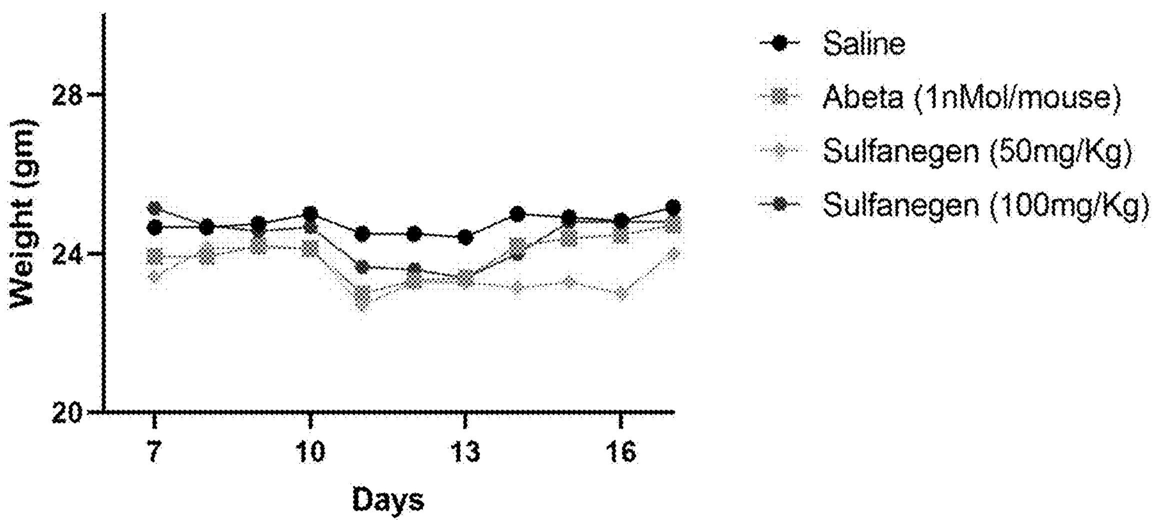
FIG. 1 shows data from Example 1.

The term, "disease or condition that is associated with decreased activity of $H_2S$ in an animal" includes any disease or condition that can be treated by increasing the level of $H_2S$ in an animal. For example, the term includes neurodegenerative diseases, such as, Alzheimer's disease, Parkinson's disease, Huntington's disease, and Cognitive Impairment. The term also includes non-alcoholic fatty liver disease (NAFLD) and non-alcoholic steatohepatitis (NASH). The term does not include cyanide poisoning.

The term "animal" includes mammals and humans. In one embodiment, the animal has been diagnosed with a disease or condition that is associated with decreased activity of $H_2S$. In one embodiment, the animal is not suffering from cyanide poisoning. In one embodiment, the compound or the pharmaceutically acceptable salt thereof is not administered to treat cyanide poisoning. In one embodiment, the compound or the pharmaceutically acceptable salt thereof is not administered to prevent cyanide poisoning in an animal that may have an above average expectation of being exposed to elevated levels of cyanide within 48 hours following administration.

Compounds and pharmaceutically acceptable salts capable of releasing 3-mercaptopyruvate in vivo are described in International Patent Application Publication Number WO 2008/005806 and by Patterson S. E., et al., Ann N Y Acad Sci. 2016 June; 1374(1): 202-209. These compounds and salts include compounds of formulae (I-VII) and pharmaceutically acceptable salts thereof:

a compound of formula (I)

(I)

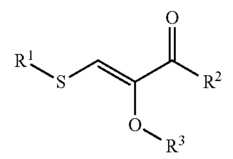

or a pharmaceutically acceptable salt thereof, wherein:

$R^1$ represents a (1-6C)alkoxycarbonyl group or a (1-6C)alkanoyl group that may bear one, two or three substituents selected from hydroxy, (1-6C)alkoxy, (1-6C)alkanoyloxy, carboxy and (1-6C)alkoxycarbonyl;

$R^2$ represents a hydroxyl group, a (1-6C)alkoxy group, $NR_aR_b$ (wherein each $R_a$ and $R_b$ is independently H or (1-6C)alkyl), or a residue of an amino acid; and $R^3$ represents a (1-6C)alkanoyl group that may bear one, two or three substituents selected from hydroxy, (1-6C)alkoxy, (1-6C)alkanoyloxy, carboxy and (1-6C)alkoxycarbonyl.

a compound of formula (II)

(II)

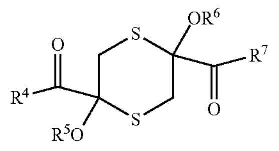

or a pharmaceutically acceptable salt thereof, wherein:

each of $R^4$ and $R^7$ independently represents a hydroxyl group, a (1-6C)alkoxy group, $NR_aR_b$ (wherein each $R_a$ and $R_b$ is independently H or (1-6C)alkyl), or a residue of an amino acid; and each of $R^5$ and $R^6$ independently represents a hydrogen atom or a (1-6C)alkanoyl group that may bear one, two or three substituents selected from hydroxy, (1-6C)alkoxy, (1-6C)alkanoyloxy, carboxy and (1-6C)alkoxycarbonyl.

a compound of formula (III)

(III)

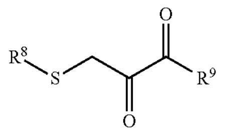

or a pharmaceutically acceptable salt thereof, wherein:

$R^8$ represents a (1-6C)alkoxycarbonyl group or a (1-6C)alkanoyl group that may bear one, two or three substituents selected from hydroxy, (1-6C) alkoxy, (1-6C)alkanoyloxy, carboxy and (1-6C) alkoxycarbonyl; and $R^9$ represents a hydroxyl group, a (1-6C)alkoxy group that may bear one, two or three substituents selected from hydroxy, (1-6C)alkoxy, (1-6C)alkanoyloxy, amino, (1-6C)alkylamino, di-(1-6C)alkylamino, carboxy and (1-6C)alkoxycarbonyl, $NR_aR_b$ (wherein each $R_a$ and $R_b$ is independently H or (1-6C)alkyl), or a residue of an amino acid.

a compound of formula (IV)

(IV)

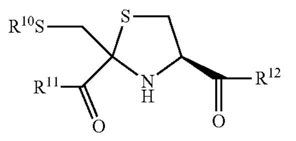

or a pharmaceutically acceptable salt thereof, wherein:

$R^{10}$ represents a hydrogen atom, a (1-6C)alkoxycarbonyl group or a (1-6C)alkanoyl group that may bear one, two or three substituents selected from hydroxy, (1-6C)alkoxy, (1-6C)alkanoyloxy, carboxy and (1-6C)alkoxycarbonyl; and one of $R^{11}$ and $R^{12}$ represents a (1-6C)alkoxy group, $NR_aR_b$ (wherein each $R_a$ and $R_b$ is independently H or (1-6C)alkyl), or a residue of an amino acid, and the other of $R^{11}$ and $R^{12}$ represents a hydroxy group, a (1-6C)alkoxy group, $NR_aR_b$ (wherein each $R_a$ and $R_b$ is independently H or (1-6C)alkyl), or a residue of an amino acid.

a compound of formula (V):

(V)

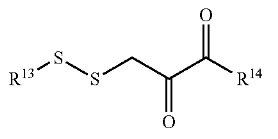

or a pharmaceutically acceptable salt thereof, wherein:

$R^{13}$ represents $R^{15}C(=O)C(=O)CH_2$ or $R^{16}C(=O)CH(NHR^{17})CH_2$ or a glutathione residue;

$R^{14}$ represents a hydroxyl group, a (1-6C)alkoxy group, $NR_aR_b$ (wherein each $R_a$ and $R_b$ is independently H or (1-6C)alkyl), or a reside of an amino acid;

$R^{15}$ represents a hydroxyl group or a (1-6C)alkoxy group;

$R^{16}$ represents a hydroxyl group or a (1-6C)alkoxy group; and $R^{17}$ represents a hydrogen atom or a (1-6C)alkanoyl group that may bear one, two or three substituents selected from hydroxy, (1-6C)alkoxy, (1-6C)alkanoyloxy, carboxy and (1-6C)alkoxycarbonyl;

a compound of formula (VI):

(VI)

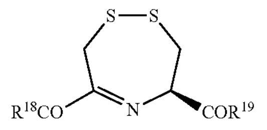

or a pharmaceutically acceptable salt thereof, wherein:

$R^8$ and $R^{19}$ each independently represents a hydroxyl group, a (1-6C)alkoxyl group, $NR_aR_b$ (wherein each $R_a$ and $R_b$ is independently H or (1-6C)alkyl), or a residue of an amino acid;

a compound of formula (VII)

(VII)

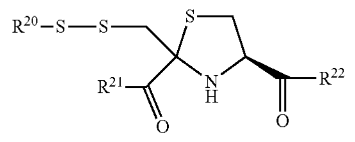

or a pharmaceutically acceptable salt thereof, wherein:

$R^{20}$ represents a group of formula $HOOCCH(NH_2)CH_2$ or

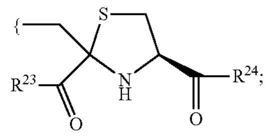

and $R^{21}$, $R^{22}$, $R^{23}$ and $R^{24}$ are each independently selected from a hydroxyl group, a (1-6C)alkoxy group, $NR_aR_b$ (wherein each $R_a$ and $R_b$ is independently H or (1-6C) alkyl), and an amino acid residue.

As used herein, the term "amino acid residue" signifies an amino acid group linked through the amino group of the amino acid to a carbonyl group. An example of an amino acid is glycine.

The term "glutathione residue" signifies a group of formula

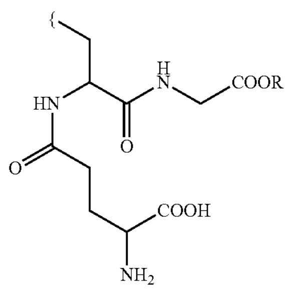

in which R represents a hydrogen atom or a (1-6C)alkyl group. Examples of particular values for a glutathione residue are $HO_2CCH_2NHCOCH(NHCOCH_2CH_2CH(NH_2)COOH)CH_2$ and $EtO_2CCH_2NHCOCH(NHCOCH_2CH_2CH(NH_2)COOH)CH_2$.

Unless otherwise indicated, an alkyl group in a (1-6C) alkyl, (1-6C)alkoxy or (1-6C)alkanoyl group may be branched or unbranched, and two branches may join to form a ring, as for example in cyclopropylmethyl.

It will be appreciated that the compounds of formula (I) may exist in the form of geometric isomers. The present invention provides both the (E) and the (Z) isomers. In one embodiment, the compound of formula (I) is in the (E) configuration.

Particular compounds and pharmaceutically acceptable salts include:

for a compound of formula (I):

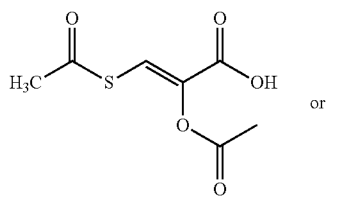

or

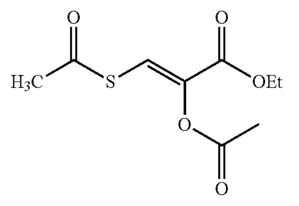

or a pharmaceutically acceptable salt thereof, for a compound of formula (II):

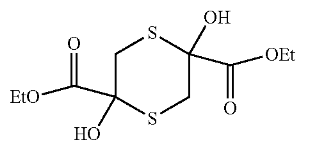 [SMILES: CCOC(=O)C1(O)CSC(O)(C(=O)OCC)CS1]

or a pharmaceutically acceptable salt thereof, for a compound of formula (III):

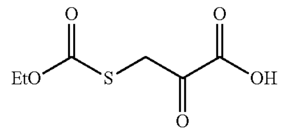 [SMILES: CCOC(=O)SCC(=O)C(=O)O]

or a pharmaceutically acceptable salt thereof; and for a compound of formula (IV):

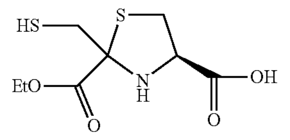 [SMILES: CCOC(=O)C1(CS)N[C@H](C(=O)O)CS1]

or a pharmaceutically acceptable salt thereof.

Further examples of compounds capable of releasing 3-mercaptopyruvate are compounds of formulae:

5

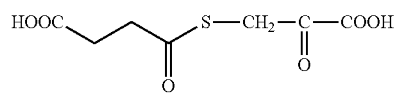

6

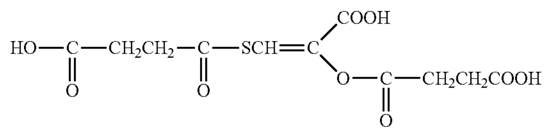

7

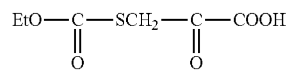

8

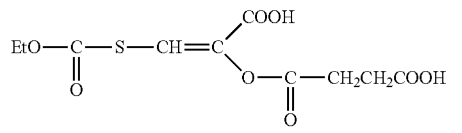

9

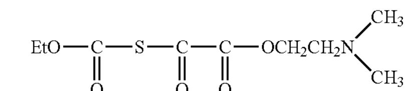

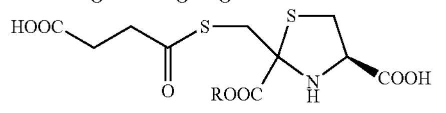

10a (R = H)
b (R = Et)

11

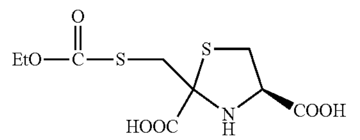

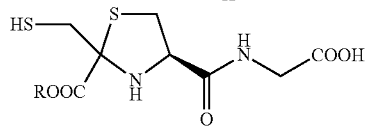

12a (R = H)
b (R = Et)

-continued

13

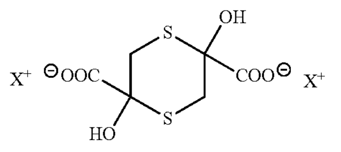

X = Na, $H_3NCH_2CH_2OH$, 1/2 $NH_4$, $(CH_3)_3NCH_2CH_2OH$, $(CH_3)_3NCH_2COOH$

14

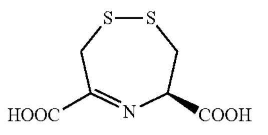

15

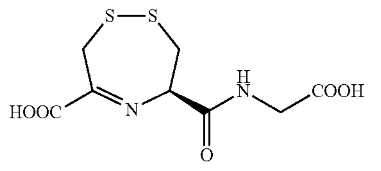

16

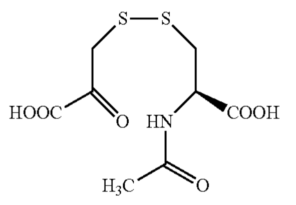

17

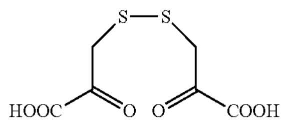

19

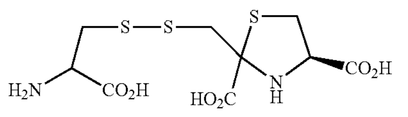

20

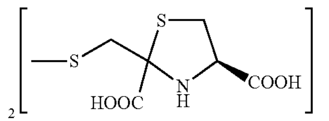

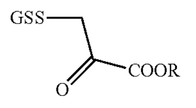

21a (R = H)
b (R = Et)
G = Glutathione residue

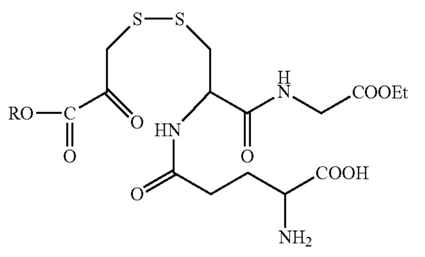

22a (R = H)
b (R = Et)

-continued

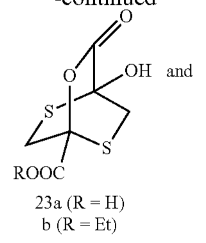

and 23a (R = H)
b (R = Et)

24

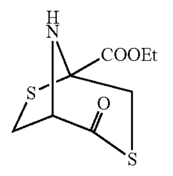

Compound 13, (a compound of formula (II) in which $R^4$ and $R^7$ each represent hydroxyl groups atoms, and $R^5$ and $R^6$ each represent hydrogen) is known from Cooper et al., J. Biol. Chem., (1982), 257, 816-826. Compound 14, (a compound of formula (VI) in which $R^{18}$ and $R^{19}$ each represents a hydrogen atom) is known, for example from Cavallini D, et al., Advances in Experimental Medicine and Biology (1982), 148, 359-74. Compound 17, (a compound of formula (V) in which $R^{13}$ represents $HOOCCOCH_2$ and $R^{14}$ represents a hydroxyl group), is also known, for example from Meister et al., Journal of Biological Chemistry (1954), 206, 561-75.

In one embodiment, the compound or the pharmaceutically acceptable salt thereof is administered orally.

In one embodiment, the compound or the pharmaceutically acceptable salt thereof is administered by injection.

In one embodiment, the compound or the pharmaceutically acceptable salt thereof is administered by ip injection or by im injection.

In one embodiment, the compound or the pharmaceutically acceptable salt thereof is not administered by injection.

The term "animal in need thereof" includes animals that have been diagnosed with a disease or condition that is associated with decreased activity of $H_2S$ as well as animals that have been identified as having an above average likelihood of contracting a disease or condition that is associated with decreased activity of $H_2S$. In one embodiment, the "animal in need thereof" is an animal that has been diagnosed with a disease or condition that is associated with decreased activity of $H_2S$. In one embodiment, the "animal in need thereof" is an animal that has been diagnosed as having an above average likelihood of contracting a disease or condition that is associated with decreased activity of $H_2S$.

In one embodiment, a pharmaceutically acceptable salt is administered. The preparation of numerous pharmaceutically acceptable salts of a compound of formula (II) is described in U.S. Pat. No. 8,757,354.

In one embodiment, a sodium salt of the compound of formula (II) is administered.

The term "effective amount" refers to a dose required to prevent the development of a disease or condition that is associated with decreased activity of $H_2S$ or to a dose required to reduce or eliminate one or more of the symptoms of a disease or condition that is associated with decreased activity of $H_2S$.

The compound or salt may be administered, e.g., im, iv, io, or po (orally), in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should generally contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose, or aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound or salt may also be administered intravenously (iv), intraperitoneally (ip), intraosseously (io), or intramuscularly (im) by infusion or injection, e.g., using an autoinjector. The compounds may be administered using an autoinjector. Solutions of the active compound can be prepared in water, optionally mixed with a nontoxic surfactant. Dispersions can also be prepared in glycerol, liquid polyethylene glycols, triacetin, and mixtures thereof and in oils. The active compounds can also be formulated as nanoparticle suspensions. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound or salt in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages can be determined by comparing in vitro activity and in vivo activity in animal models. Methods for the extrapolation of effective dosages in mice, and other animals, to humans are known to the art; for example, see U.S. Pat. No. 4,938,949.

The amount of a compound or salt required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound or salt to treat or prevent a disease or condition that is associated with decreased activity of $H_2S$ may be determined using pharmacological models which are well known to the art, or using the models described in the Examples below.

The invention will now be illustrated by the following non-limiting Examples.

EXAMPLES

Example 1 Treatment of Neurodegenerative Disorders: Efficacy of Sulfanegen in i.c.v Aβ1-42 Injected Nontransgenic Mice Eight-week old Wild type C57/BL6 mice were treated i.p. with sulfanegen at 50 and 100 mg/kg dose during the entire duration of experiment. The mice were injected with intracerebroventricular (i.c.v) Aβ1-42 on day 3 after initiation of drug treatment (1 nmol/mouse). Behavioral test (T-maze) was conducted 6 days after Aβ1-42 injection, which was followed by euthanization on day 8. Biochemical analysis of the collected brain tissues was conducted using ELISA method for quantitation of Aβ1-42, and immunohistochemical analysis for GFAP (inflammatory marker). The brain tissues were also analyzed for oxidative stress markers (GSH assay, see Example 5; and protein carbonyls, see Example 6).

Groups:

Saline control N=12, (N=5 study 2; N=7 study 3)

Abeta control N=15, (N=7 study 2; N=8 study 3)

Sulfanegen, 50 mg/kg, N=7

Sulfanegen, 100 mg/kg, N=7

Decrease in body weights was observed in the mice after i.c.v Abeta injections in all groups, followed by a gradual recovery. No marked decrease or increase in weights was observed in the sulfanegen treated group compared to Aβ1-42-only control group (FIG. 1). Two mice (out of 7) in sulfanegen 100 mg/kg i.p. group died during the course of this experiment. Sulfanegen at dose 50 mg/kg i.p. was well tolerated by the animals. No other signs of distress were observed in sulfanegen treated mice at both the tested doses. Data is shown in FIG. 1.

Example 2 T-Maze Experimental Protocol

Spontaneous alternation in a T-maze was used to assess working memory abilities, based on the innate tendency of mice to alternate their choice of a goal arm based on their recall of the initial choice. The T-maze used was made of black plexiglass as per dimensions stated in Nat Protocol, 2006 [Deacon, R. M., et al., Nat. Protoc. 2006, 1 (1), 7-12]. Mice were placed in the start arm with the central divider in place so that when entering either of the goal arms the mice were not able to see the other one. The mice were allowed to move freely in the whole hall, and then, after being confined to the start arm for 30 seconds, the animal was allowed to move freely for a total of 15 arm entrees. Mice that did not complete the task or took more than 30 minutes to complete the task were excluded. The alternation percentage was calculated by dividing the number of times the animal entered alternating arms by 14 (free-choice trials). An arm entry is defined as the animal's tail tip entering the arm and repetitive arm entries as an animal re-entering the same arm three times in a row (e.g., 5 sequential entries into the same arm is 3 repetitive entries). Ratio of right and left arm entries was calculated to determine spatial preference of mice in different treatment groups. The data were analyzed using repeated measures analysis of variance (ANOVA) using Dunnett test.

Figure 2:
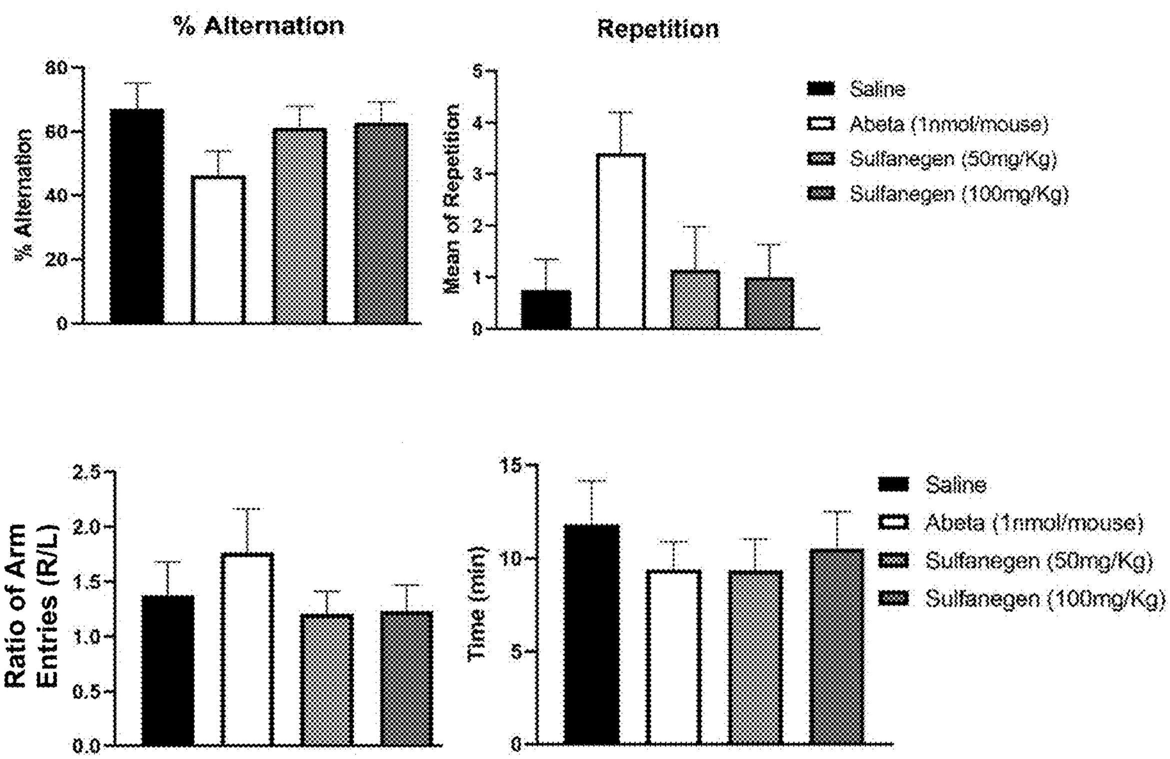
FIG. 2 shows data from Example 2.

Saline group showed the highest alternation and the lowest repetition rate. Conversely, Aβ1-42-only control group showed reduced alternation while having highest repetition rate. Sulfanegen treated mice exhibited alternation and repetition behavior similar to that of the saline treated group. There was no statistically significant difference between the two doses of sulfanegen (50 mg/Kg and 100 mg/Kg) used in this study (FIG. 2).

No statistically significant difference was seen for arm entry in the T-maze between different treatment groups. No statistically significant difference was observed between the treatment groups for the total time taken to complete the T-maze test. Thus, sulfanegen at both doses 50 and 100 mg/kg, showed a marked improvement in cognitive behavior pattern as determined by the T-maze spontaneous alternation. The percent alternation and repetition pattern in sulfanegen treated groups demonstrated significant improvement when compared to the amyloid beta-only control group. No statistically significant difference was observed in the cognitive improvement offered by sulfanegen at 50 mg/kg and 100 mg/kg dose.

Example 3 TNFα Assay

TNFα ELISA kit (BMS607HS, invitrogen) was used. Brain tissue samples were assayed in duplicate. Briefly, the strips provided in the kit were washed with 400 μL wash buffer (lx) twice. 50 μL of brain homogenates or standards were added to 50 μL sample diluent (PBS) in each well. This was followed by addition of 50 μL Biotin conjugate and the wells were incubated for 2 hours at room temperature with shaking. The wells were washed 6 times before addition of 100 μL Streptavidin-HRP to all wells. Treatments with amplification solutions and TMB substrates followed. The samples were read at 450 nm. Quantification of TNFα in each well was conducted using the standard curve and was normalized to the weight of brain tissue.

Sulfanegen is a prodrug of 3-mercaptopyruvate (3-MP), the substrate for mercaptopyruvate sulfurtransferase (MST). MST reacts with 3-MP to convert a protein-cysteine residue to an unstable persulfide-containing intermediate. This intermediate susceptible to reduction to release hydrogen sulfide. $H_2S$ has been reported to have anti-inflammatory effects. Since neuronal inflammation is a major component of AD, pro-inflammatory cytokines such as TNFα and IL-6 were measured in sulfanegen-treated mice.

Figure 3:
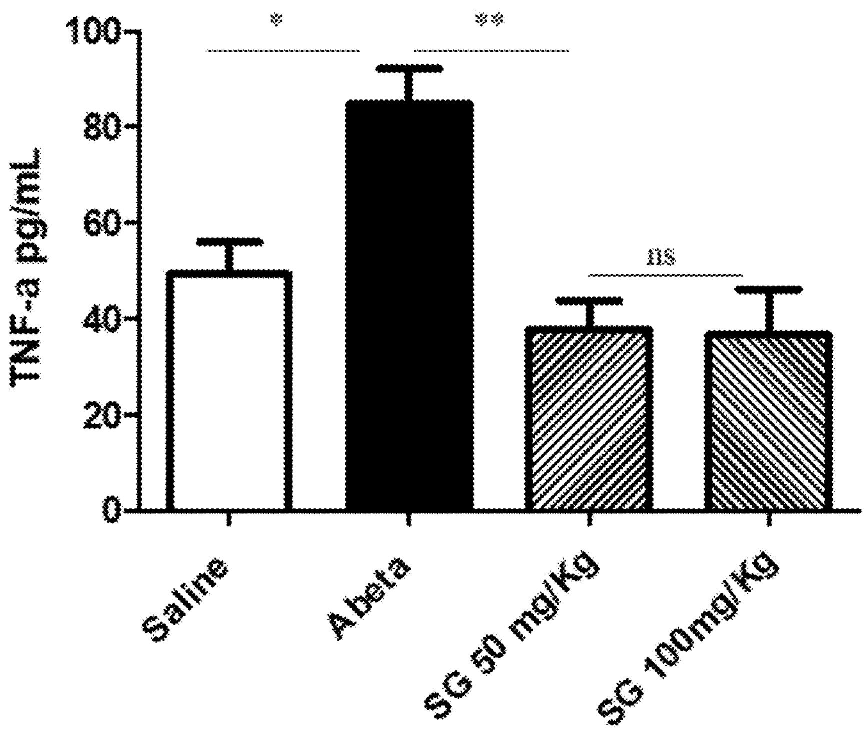
FIG. 3 shows data from Example 3. Effect of sulfanegen treatment on inflammatory marker, TNFα. Statistical analysis showed significant difference between saline, Abeta (within the study group) and sulfanegen treated groups. No significant difference was observed between the sulfanegen groups (50 mg/kg vs 100 mg/kg). Values normalized to protein concentration determined by BCA protein assay. Upper panel shows the absolute data, while lower panel shows fold changes with respect to saline control.
Figure 3:
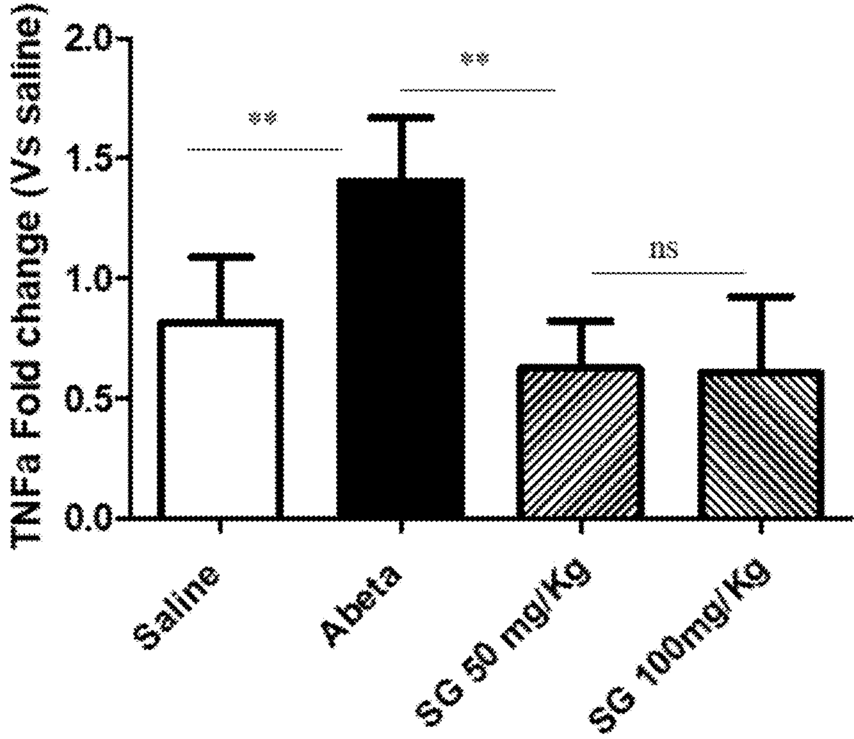

TNFα ELISA assay showed a significant decrease in inflammation (e.g., TNFα level) in the sulfanegen treated groups, however, the response appears to be saturated response (no difference between animals treated with 50 mg/Kg and 100 mg/Kg) (FIG. 3).

Example 4 IL-6 Assay

IL-6 ELISA (BMS603HS, invitrogen) was used. Brain tissue samples were assayed in duplicate. Briefly, the strips provided in the kit were washed with 400 μL wash buffer (lx) twice. 50 μL of brain homogenates or standards were added to 50 μL sample diluent (PBS) in each well. This was followed by addition of 50 μL Biotin conjugate and the wells were incubated overnight at 4° C. with shaking. The wells were washed 6 times before addition of 100 μL Streptavidin-TRP to all wells. Treatments with amplification solutions and TMB substrates followed. The samples were read at 450 nm (reference wavelength 620 nm). Quantification of IL-6 in each well was conducted using the standard curve and was normalized to the weight of brain tissue.

Figure 4:
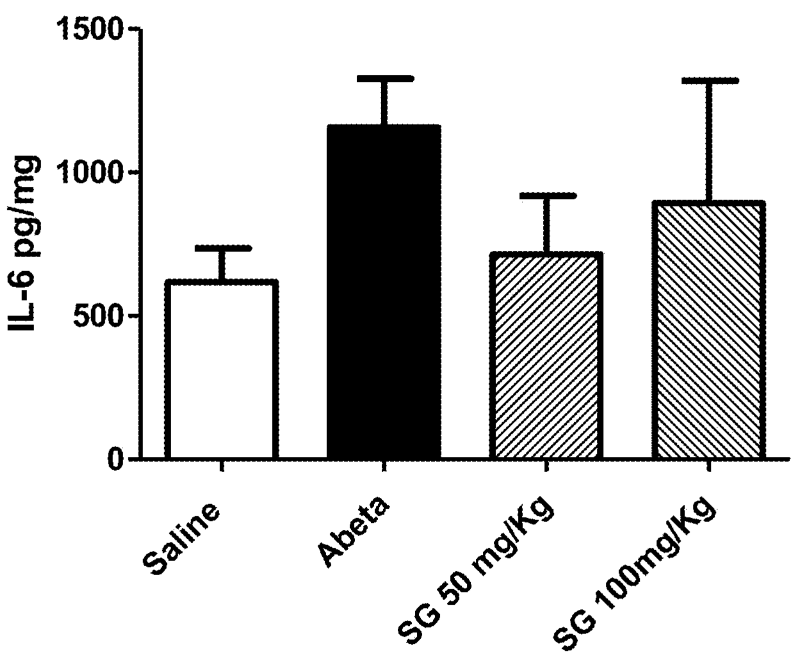
FIG. 4 shows data from Example 4. Effect of sulfanegen treatment on inflammatory marker, TL6. Increase in IL-6 was seen in Amyloid beta and Sulfanegen group at 100 mg/Kg. Statistical analysis showed significant difference between saline, Abeta and sulfanegen (50 mg/kg) groups. Values normalized to protein concentration determined by BCA protein assay. Upper panel shows the absolute data, while lower panel shows fold changes with respect to saline control.
Figure 4:
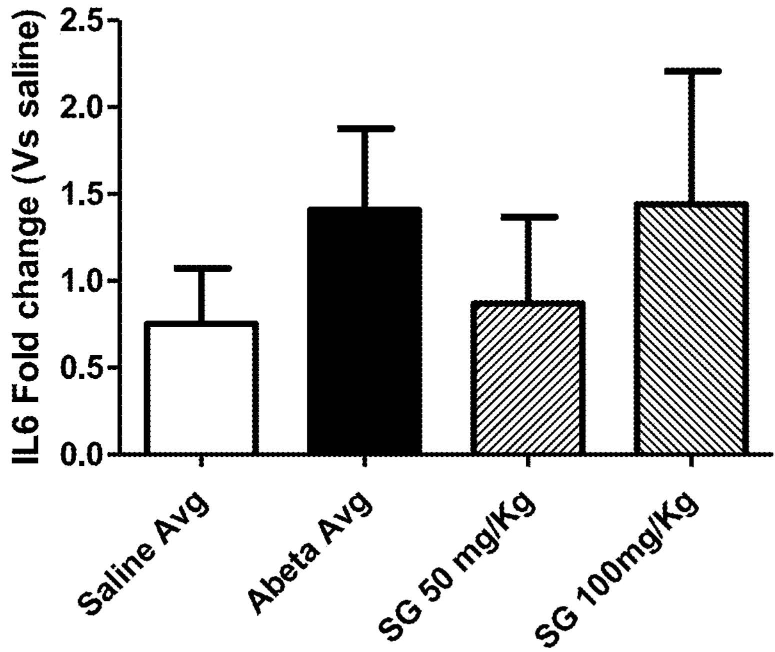

Increase in IL-6 was seen in amyloid-beta only treated group and sulfanegen (100 mg/kg) treatment group. A reduction of increased IL-6 levels similar to the reduction for TNFα was observed in amyloid-beta treated mice after sulfanegen treatment in 50 mg/kg group (FIG. 4). This indicates anti-inflammatory activity of sulfanegen.

Example 5 Glutathione (GSH) and GSSG Level

Figure 8A:
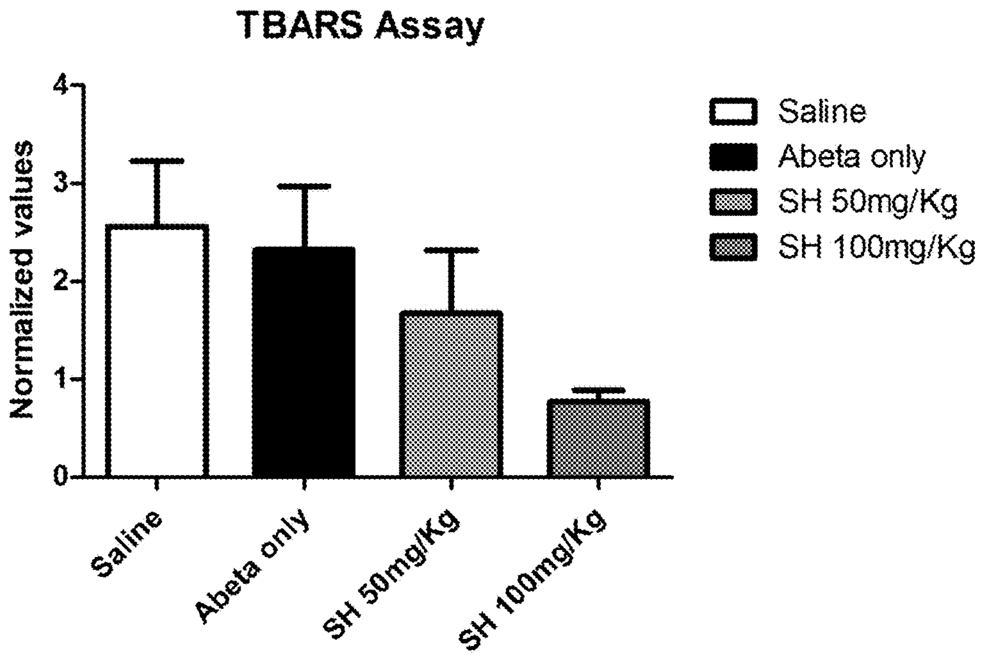
FIGS. 8A-8C. Quantitation of oxidative stress markers in the brain tissues of mice (icy injected with Abeta) treated with or without sulfanegen (labeled SH) at 50 or 100 mg/Kg. Levels of all the oxidative stress markers; GSH, protein carbonyls and TBARS (lipid peroxidation) are significantly reduced in the mice treated with sulfanegen.
Figure 8B:
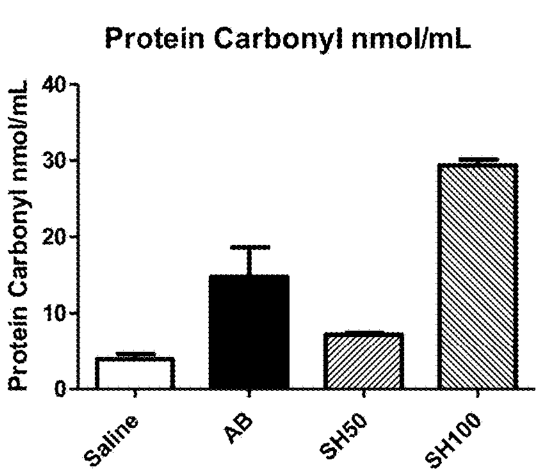
Figure 8C:
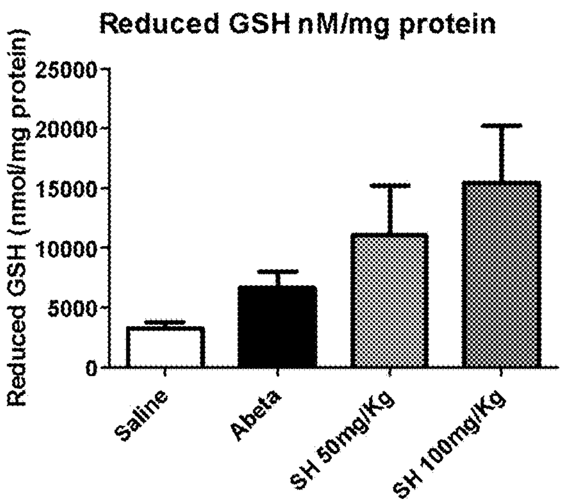

The brain GSH and GSSG level were measured with Glutathione assay kit (Cayman Chemical, Ann Arbor, MI) using the i.c.v Abeta mouse model (see Example 1). A total of 50 μl of sample was added to each well, and 150 μl the assay cocktail (MES buffer, reconstituted cofactor mixture, enzyme mixture, water, and DTNB) were added to the wells. The absorbance was measured at 414 nm using Spectra Max M5 microplate reader. Assay range was calculated under the standard curve (0-16 μM GSH or 0-8 μM GSSG). Results were expressed as nmol/mg protein and ratio of GSH/GSSG. Data is shown in FIG. 8C. Total GSH levels were higher in sulfanegen treated groups at both doses 50 mg/Kg and 100 mg/Kg. Samples from icv amyloid beta group showed significantly higher GSSG levels compared to vehicle treated samples. Reduced GSH levels were significantly higher in sulfanegen group (100 mg/Kg) compared to both vehicle and amyloid beta treatment. Reduced GSH levels were slightly lower in vehicle treated group compared to the amyloid treatment but not statistically significant.

Example 6 Protein Carbonyl Assay

The protein carbonyl content is used as a marker of protein oxidation in the i.c.v Abeta mouse model (see Example 1). The amount of protein-hydrozone produced is quantified spectrophotometrically by Protein Carbonyl Colorimetric assay kit (Cayman Chemical, Ann Arbor, MI). 100 μl of sample was transferred into two tubes, one containing 400 μl of DNPH and the other tube containing 400 μl of 2.5 M HCl. Both tubes were incubated in the dark at room temperature for one hour. After incubation, 500 μl of 20% TCA was added to each tube, placed the tubes on ice and incubated for five minutes. The tubes were centrifuged at 10,000 g for 10 min at 4° C., the pellet was resuspended in 500 μl of 20% TCA, and centrifuged the tubes at 10,000 g for 10 min at 4° C. The pellet obtained was resuspended in 500 μl of (1:1) Ethanol/Ethyl Acetate mixture and centrifuged at 10,000 g for 10 min at 4° C., this step was repeated two more times. After the final wash, the protein pellets were resuspended in 500 μl of guanidine hydrochloride with vortex, centrifuged at 10,000 g for 10 min at 4° C., and then transferred to a 96-well plate. The absorbance was measured at 385 nm using Spectra Max M5 microplate reader. Data is shown in FIG. 8B. Levels of protein carbonyls as the oxidative stress marker, were significantly increased in icv Aβ treated group and were significantly reduced in the mice treated with 50 mg/kg sulfanegen.

Example 7 Lipid Peroxidation Assay

The extent of lipid peroxidation, in the i.c.v Abeta mouse model (see Example 1), was correlated to the levels of thiobarbituric (TBA) acid-reactive entities (TBARS assay). Homogenized brains were exposed to TBA—trichloroacetic acid (TCA)—chloridic acid reagent (HCl; 0.37% TBA, 0.25 N HCl, and 15% TCA) (1:1:1, 2 mL) and incubated for 15 minutes at ambient temperature. Centrifugation of the incubate was followed by measurement of the absorption of the supernatant at 535 nm against a blank reference. Total protein was determined through the BCA protein assay. TBARS were then proportioned to total protein content and represented as percentage of the values in saline-treated nontransgenic control mice. Data is shown in FIG. 8A. Levels of TBARS (lipid peroxidation) as the oxidative stress marker are significantly reduced in the mice treated with 50 and 100 mg/Kg sulfanegen.

Example 8 Cell Culture Studies—In Vitro Amyloid Toxicity Protection Assay

SH-SY-5Y cells were seeded at a density of 20000/well in a 96-well plate and incubated overnight at 37° C. Following day, cells were treated with media according to their respective treatment group in triplicate. Vehicle-only treated cells are used as control groups. After 24 hours, cells were incubated with 20 μM of Amyloid beta Aβ1-42 (Genscript) and treated with their respective treatment groups. On day 3, Cells were incubated with media containing CCK-8 (<10%). After 3 hours of incubation, the absorbance is measured at 450 nm (reference wavelength 600 nm) using Me5 plate reader (Spectramax). The final volume in a well is kept at 100 μL CCK-8 (CK04, Dojindo labs) in this assay.

Figure 5:
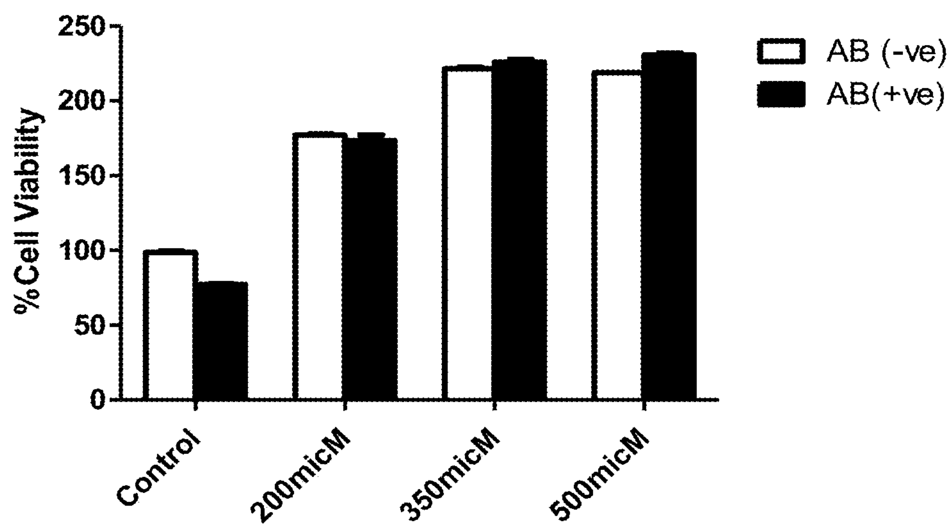
FIG. 5 shows data from Example 8.
Figure 6:
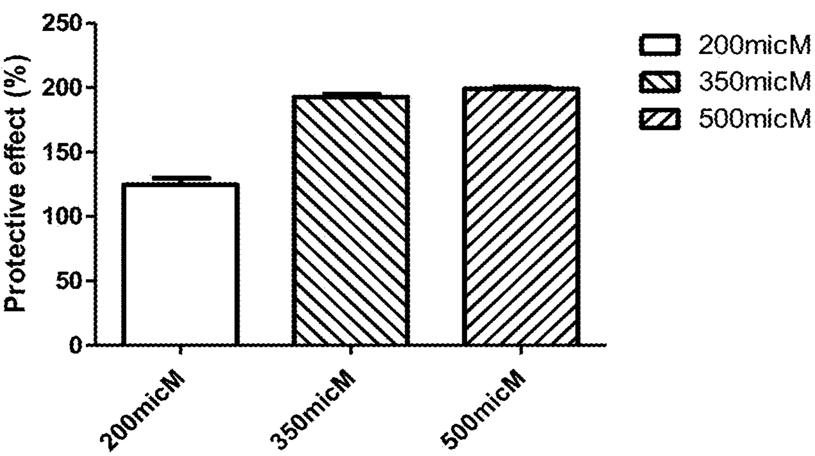
FIG. 6 shows data from Example 8.

Amyloid beta (20 μM) treatment resulted in 25% reduction in cell viability. This reduction in cell viability was prevented by sulfanegen treatment. Furthermore, treatment with sulfanegen caused increase in cell growth, even above the control levels. Thus, Amyloid protection assay shows a high protective effect for sulfanegen against Aβ1-42 cytotoxicity, but the effect appears to be saturated at doses above 350 μM (no difference at higher 500 μM dose) (FIGS. 5 and 6).

Example 9 Efficacy of Sulfanegen in APP/PS1 Transgenic Mice

In another study, 7 and 12 month cohorts of APP/PS1 mice (N=5-7/group, both male and female mice, about 1.5:1-1:2 male/female ratio was used for each experimental group) were treated with sulfanegen (75 mg/kg) for 12 weeks by intraperitoneal administration. Cognitive assessment of these mice was conducted 12 weeks after treatment using T-maze, followed by euthanization at the end of 12 weeks and collection of brain tissues for biochemical and histopathological analysis.

Both sexes were combined for data analysis. One-way ANOVA was used for statistical analysis (Bonferroni correction for multiple comparisons). Significance represented is with respect to Saline Tg group.

Figure 11:
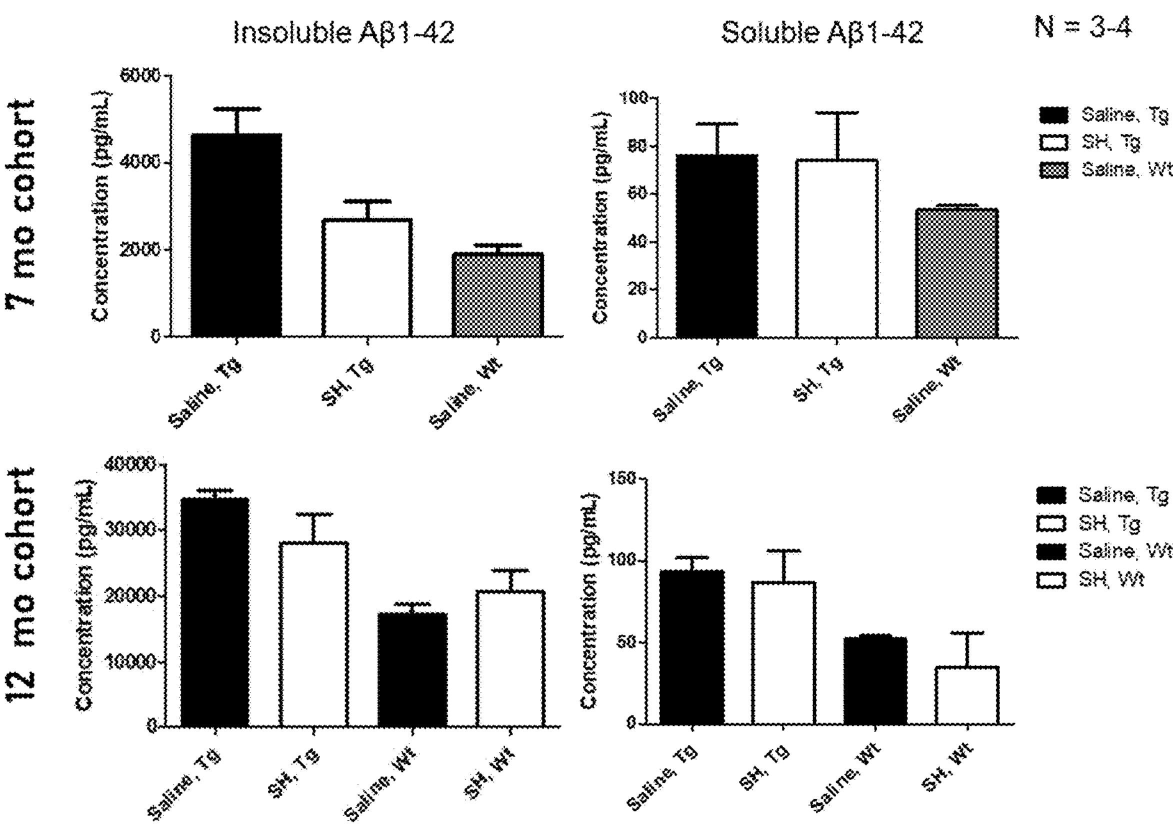
FIG. 11 shows data from Example 11.

Biochemical analysis data are shown in, for example, FIG. 11 (see Examples 10-11 below).

Figure 9:
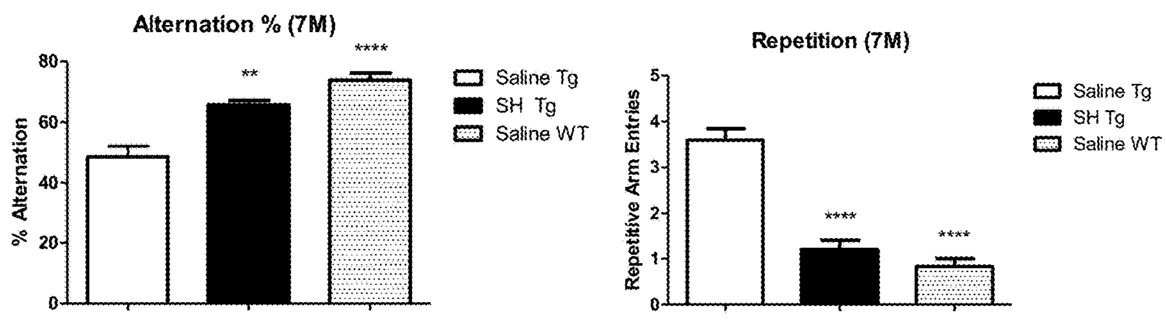
FIG. 9 shows data from Example 9 (7-month cohort).
Figure 9:
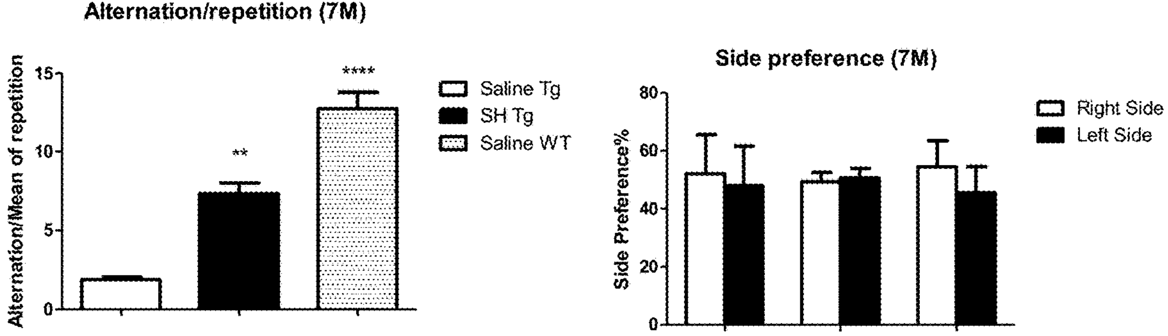
Figure 10:
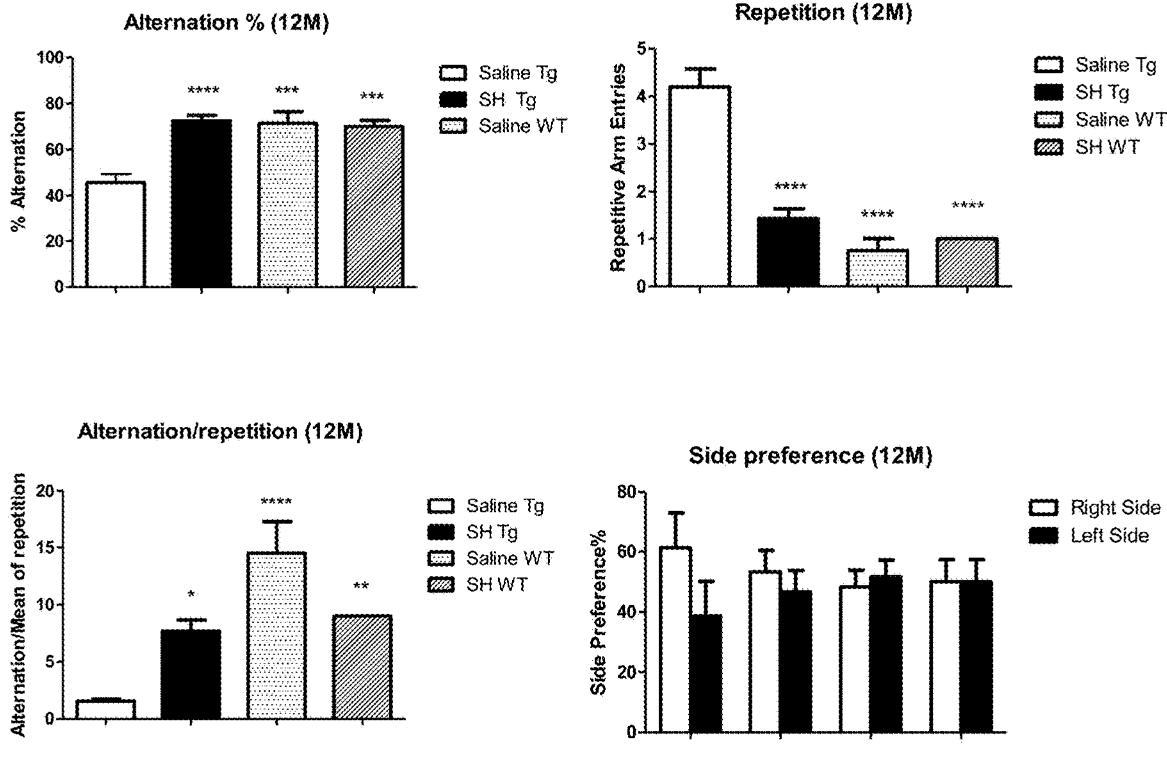
FIG. 10 shows data from Example 9 (12-month cohort).

Cognitive assessments data are shown in FIG. 9 (7-month cohort) and FIG. 10 (12-month cohort). T-maze spontaneous alternation was used to assess cognitive function. The data shows improved cognitive function in both mice models treated with sulfanegen, even when the treatment was initiated at later stages of the disease in the transgenic (Tg) mice model, indicating both potential preventative and therapeutic benefits.

Example 10 Biochemical Analysis

After behavioral tests, all the mice were sacrificed and the brain was immediately removed. The half of brain tissue were fixed in 4% paraformaldehyde solution for histopathology, other half was stored at −80° C. for the biochemical studies.

The brain tissue for biochemical analysis was rapidly homogenized in these buffers 1) TBS (20 mM Tris-HCl and 150 mM NaCl) buffer with protease inhibitors and 5 M Guanidine-HCl in 50 mM Tris-HCl buffer for Aβ1-42 ELISA assay (FIG. 11, see Example 11 below), 2) 50 mM MES buffer for GSH (FIG. 8C, see Example 5) and Protein Carbonyl assay (FIG. 8B, see Example 6), 3) RIPA buffer with protease inhibitors for TBARS assay (FIG. 8A, see Example 7). And then the homogenates were centrifuged at 10,000 g at 4° C. for 20 minutes. The supernatant was collected and was used to measure according to the manufacturer's directions.

Example 11 $Aβ^{1-42}$ ELISA Assay

The $Aβ^{1-42}$ in the brain was measured using a sensitive and specific ELISA assay according to the manufacturer's instructions (Immuno-Biological Laboratories Co., Ltd., Japan). A total of 100 μl of sample was added to each well, and then the plate was incubated overnight at 4° C. After several washes, 100 μl of labeled antibody was added to each well, and the plate was incubated at 4° C. for 1 hour. After several washes, the chromogen (100 μl) was added, followed by incubation for 30 min at room temperature in the dark. The reaction was stopped after adding stop solution (100 μl); the absorbance at 450 nm was detected on a Spectra Max M5 microplate reader. A standard curve with known amounts of $A\beta^{1-42}$ was also generated. The $A\beta^{1-42}$ level was calculated according to the standard curve. Data is shown in FIG. 11. Increased levels of soluble and insoluble Aβ were detected in saline treated APP/PS1 mice compared to age-matched wild type controls. Sulfanegen treatment significantly decreased insoluble Aβ levels, with negligible effect on the levels of soluble Aβ in the transgenic mice.

Example 12 Zn-Agar Entrapment for $H_2S$ Measurement in Cell Culture

Figure 7:
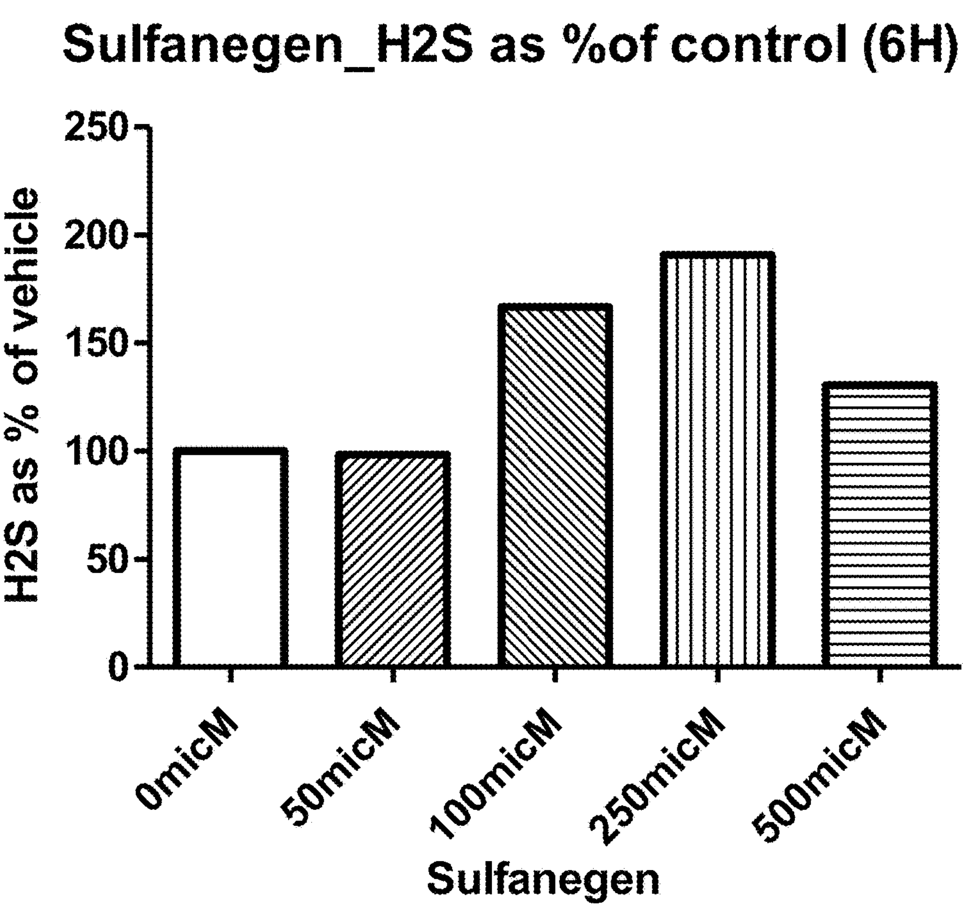
FIG. 7 shows data from Example 12. Release of $H_2S$ in cells exposed to sulfanegen. $H_2S$ release shows a dose-dependent increase up to 250 μM at 6 h and then shows a decrease at 500 μM as compared to 250 μM. The $H_2S$ release was compared against vehicle control (represented as 100% at 0 μM).

To sterilized agar solution (1% w/v) was added 45 mM Zn Acetate and 4.5 mM NaOH (both prepared in sterile water). The solution was then applied to the non-adherent surface of the empty flasks and allowed to solidify. Cells were seeded in T-25 flask at 1 million cells/flask overnight. Cells were treated with sulfanegen at 0-500 μM concentrations and incubated for 6 hours. After the incubation period, the media was removed and 2 ml N,N-dimethyl-p-phenylenediamine chloride was added to the agar layer and incubated at RT for 10 mins. This was followed by addition of 400 μL of ferrous chloride and incubation for 20 minutes. The solution was then aliquoted into 96-well plate and absorbance was measured at 670 nm. The release of $H_2S$ was measured using a standard curve generated with NaSH under similar experimental conditions (incubation with NaSH was done for 1 hr). Results are shown in FIG. 7. $H_2S$ release shows a dose-dependent increase up to 250 μM at 6 h and then shows a decrease at 500 μM as compared to 250 μM.

Example 13 Brain Permeability and Bioavailability Assessment of Sulfanegen

To ascertain the distribution of sulfanegen to the brain, plasma and brain samples were harvested from intraperitoneally treated animal groups and analyzed via LC-MS/MS. A saline solution of sulfanegen was injected into the mouse peritoneum at a dose of 50 mg/kg. Specifically, samples were collected at 0.25, 0.5, 1, 2, and 4 h after the drug administration. Once the animals failed to respond to stimuli toward their paws, blood samples were collected via cardiac puncture bleeding into EDTA coated tubes. Samples were immediately centrifuged at 3000 rpm for 10 min at 4° C., and the separated top plasma layer was transferred into a new tube. Blood samples were stored at −80° C. until LC-MS/MS analysis. For brain samples, brain tissue was extracted from the animal and washed with copious volumes of ice-cold D-PBS for removal of blood from the sample. The brain samples were homogenized by adding 1:5 (w/v) of ice-cold D-PBS into the tube and using a mechanical homogenizer on them. Homogenized brain samples were stored at −80° C.

Similar experimental design was used for determination of oral bioavailability of sulfanegen (Table 2). Plasma samples were collected after intravenous and oral administration of the compound and concentration of sulfanegen in these samples was determined using LC-MS/MS analysis. Results are shown below. Result in Table 1 suggests that sulfanegen is able to cross the blood brain barrier (BBB).

TABLE 1

| Brain-Plasma (B/P) ratio | | |
|---|---|---|
| | AUC (h*μM) | B/P Ratio |
| Brain | 51.495 | 0.751 |
| Plasma* | 68.59 | |

TABLE 2

| Oral bioavailability | | | |
|---|---|---|---|
| | dose (mg/kg) | AUC(h*umol/L) | bioavailability |
| i.v. | 10 | 32.59 | 15.10% |
| p.o. | 50 | 24.6 | |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method comprising, treating a neurodegenerative disease that is associated with decreased activity of $H_2S$ in an animal in need thereof, wherein the disease that is associated with decreased activity of $H_2S$ in an animal is Alzheimer's disease or Parkinson's disease, by orally administering to the animal, an effective amount of a compound of formula (I) and pharmaceutically acceptable salts thereof (I)

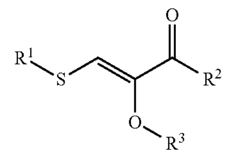

wherein:

$R^1$ represents a (1-6C)alkoxycarbonyl group or a (1-6C) alkanoyl group, wherein the (1-6C)alkoxycarbonyl group and the (1-6C)alkanoyl group may bear one, two or three substituents selected from hydroxy, (1-6C) alkoxy, (1-6C)alkanoyloxy, carboxy and (1-6C)alkoxycarbonyl;

$R^2$ represents a hydroxyl group or a (1-6C)alkoxy group; and $R^3$ represents a (1-6C)alkanoyl group that may bear one, two or three substituents selected from hydroxy, (1-6C) alkoxy, (1-6C)alkanoyloxy, carboxy and (1-6C)alkoxycarbonyl; or a compound of formula (IV) and pharmaceutically acceptable salts thereof (IV)

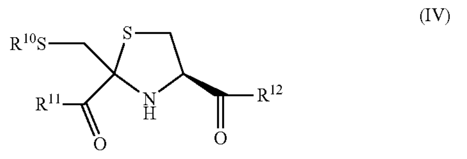

wherein:

$R^{10}$ represents a hydrogen atom, a (1-6C)alkoxycarbonyl group or a (1-6C)alkanoyl group, wherein the (1-6C) alkoxycarbonyl group and the (1-6C)alkanoyl group may bear one, two or three substituents selected from hydroxy, (1-6C)alkoxy, (1-6C)alkanoyloxy, carboxy and (1-6C)alkoxycarbonyl; and one of $R^{11}$ and $R^{12}$ represents a (1-6C)alkoxy group, and the other of $R^{11}$ and $R^{12}$ represents a hydroxy group or a (1-6C)alkoxy group.

2. The method of claim 1, wherein the animal has been diagnosed with the disease.

3. The method of claim 1, wherein the animal is not suffering from cyanide poisoning.

4. The method of claim 1, wherein the compound is a compound of formula (I).

5. The method of claim 1, wherein the compound is a compound of formula (IV).

6. The method of claim 1, wherein the compound or the pharmaceutically acceptable salt is selected from:

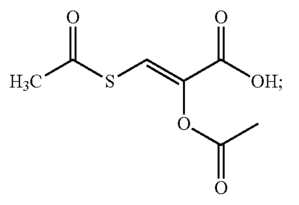

-continued

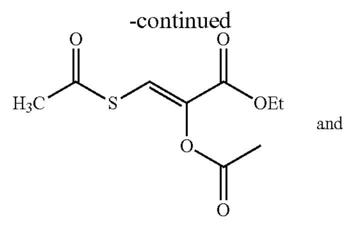

and

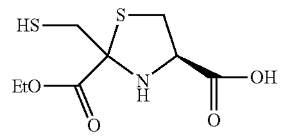

and pharmaceutically acceptable salts thereof.

7. The method of claim 1, wherein the disease that is associated with decreased activity of $H_2S$ in an animal is Alzheimer's disease.

8. The method of claim 1, wherein the disease that is associated with decreased activity of $H_2S$ in an animal is Parkinson's disease.

* * * * *